(12) United States Patent
Chen et al.

(10) Patent No.: US 10,556,798 B2
(45) Date of Patent: Feb. 11, 2020

(54) SYNTHESIS OF FLUORINATED GRAPHENE OXIDE FOR ELECTROCHEMICAL APPLICATIONS

(71) Applicant: Lakehead University, Thunder Bay (CA)

(72) Inventors: Aicheng Chen, Thunder Bay (CA); Boopathi Sidhureddy, Thunder Bay (CA); Antony Raj Thiruppathi, Thunder Bay (CA)

(73) Assignee: LAKEHEAD UNIVERSITY, Thunder Bay (CA)

( * ) Notice: Subject to any disclaimer, the term of this patent is extended or adjusted under 35 U.S.C. 154(b) by 0 days.

(21) Appl. No.: 15/869,785

(22) Filed: Jan. 12, 2018

(65) Prior Publication Data

US 2018/0251378 A1    Sep. 6, 2018

Related U.S. Application Data

(60) Provisional application No. 62/446,114, filed on Jan. 13, 2017, provisional application No. 62/508,080, filed on May 18, 2017.

(51) Int. Cl.
| | | |
|---|---|---|
| *C01B 32/198* | (2017.01) | |
| *C07D 301/00* | (2006.01) | |
| *G01N 27/48* | (2006.01) | |
| *G01N 27/416* | (2006.01) | |
| *G01N 27/30* | (2006.01) | |
| *G01N 27/42* | (2006.01) | |

(52) U.S. Cl.
CPC .......... *C01B 32/198* (2017.08); *C07D 301/00* (2013.01); *G01N 27/48* (2013.01); *G01N 27/308* (2013.01); *G01N 27/4166* (2013.01); *G01N 27/42* (2013.01)

(58) Field of Classification Search
CPC .................................................... C01B 32/198
See application file for complete search history.

(56) References Cited

PUBLICATIONS

Thiruppathi et al. Electrochemistry Communications 2017, 76, 42-46 (Year: 2017).*
Marcano et al. ACS Nano 2010, 4, 4806-4814 (Year: 2010).*

* cited by examiner

*Primary Examiner* — Matthew P Coughlin
(74) *Attorney, Agent, or Firm* — Michael R. Williams; Ryan W. Dupius; Ade & Company Inc.

(57) ABSTRACT

Doping and functionalization could significantly assist in the improvement of the electrochemical properties of graphene derivatives. Herein, we report a one-pot synthesis of fluorinated graphene oxide (FGO) from graphite. The surface morphology, functionalities and composition of the resulting FGO have been studied using various surface characterization techniques, revealing that layer-structured nanosheets with ~1.0 at. % F were formed. The carbon bound F exhibited semi-ionic bonding characteristic and significantly increased the capacitance of FGO compared to graphene oxide (GO). Further, the FGO has been employed for the simultaneous detection of heavy metal ions $Cd^{2+}$, $Pb^{2+}$, $Cu^{2+}$ and $Hg^{2+}$ using square wave anodic stripping voltammetry; and a substantial improvement in the electrochemical sensing performance is achieved in comparison with GO.

6 Claims, 3 Drawing Sheets

Figure 1:
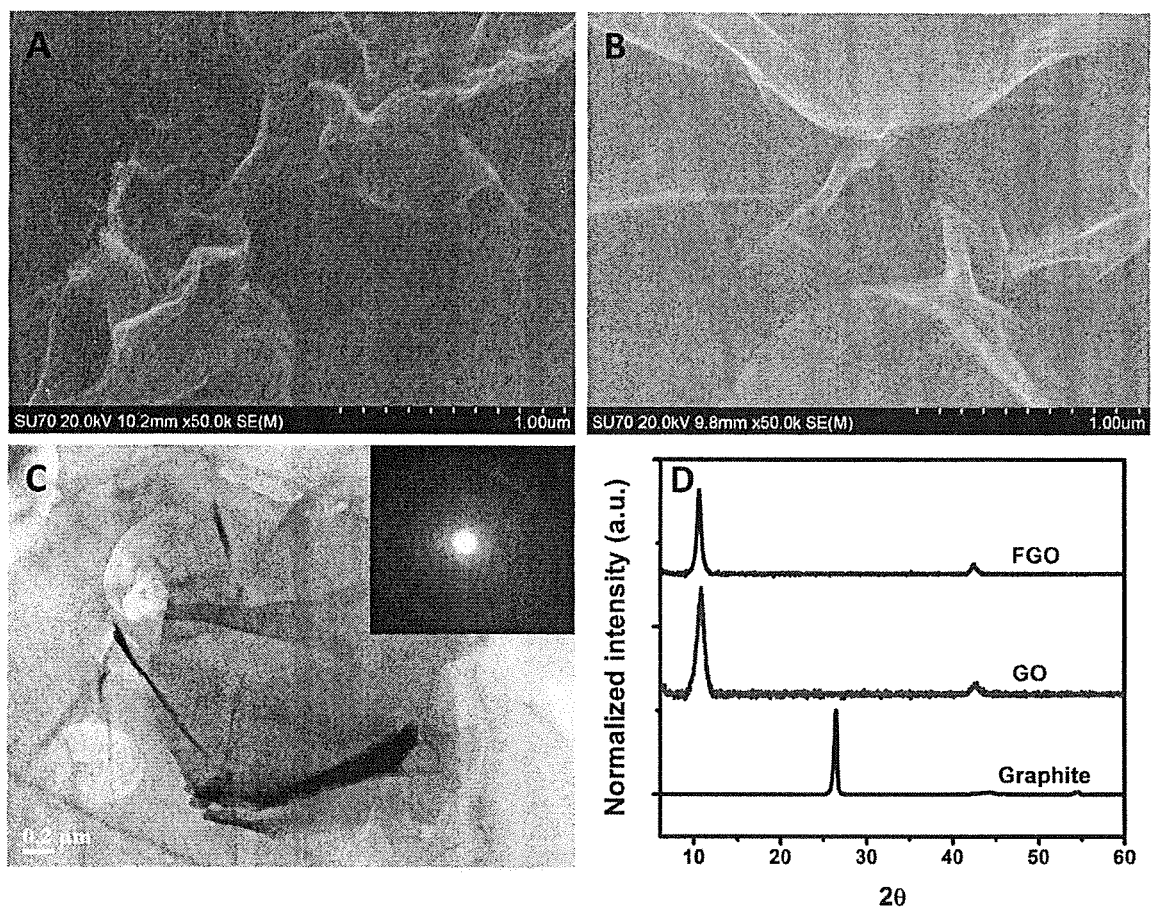

SYNTHESIS OF FLUORINATED GRAPHENE OXIDE FOR ELECTROCHEMICAL APPLICATIONS

PRIOR APPLICATION INFORMATION

The instant application claims the benefit of U.S. Provisional Patent Application Ser. No. 62/446,114, filed Jan. 13, 2017 and ‘entitled “Facile One-pot Synthesis of Fluorinated Graphene Oxide for Electrochemical Sensing of Heavy Metal Ions”, the contents of which are incorporated herein by reference.

The instant application also claims the benefit of U.S. Provisional Patent Application Ser. No. 62/508,080, filed May 18, 2017 and entitled “SYNTHESIS OF FLUORINATED GRAPHENE OXIDE FOR ELECTROCHEMICAL APPLICATIONS”, the contents of which are incorporated herein by reference.

BACKGROUND OF THE INVENTION

Electrochemical activities of pristine graphene and its derivatives are subjected to edge/basal plane doping, and functionalization [1-3]. Aside from the prevailing basal/edge plane effect, functionalization and doping of graphene highly influence the physicochemical and electrochemical properties of graphene and graphene oxide (GO) [3]. Hence, various graphene derivatives, particularly doped with heteroatoms (e.g., N, F, Cl, B and S), have been widely explored for metal-free electrocatalysis, supercapacitor, and battery applications [4-8]. Among the doped graphene based nanomaterials, F-doping has gained great attention because of unique properties such as its high temperature resistance and enhanced electrocatalytic activity [9-11]. Fluorine has a higher electronegativity than carbon, which may result in different bonding characteristics such as ionic, semi ionic and covalent [12]. In addition, the electronic structure of fluorinated graphene may be altered significantly due to its dual characteristics: (i) electron-withdrawing nature arising from the strong electronegativity of F; and (ii) electron donating nature from the lone-pair electrons [11]. Therefore, fluoro-graphene derivatives have been widely explored for a variety of applications such as batteries [5,13], biomedical devices [14], capacitors [15], and catalyst support [11]. Typically, fluorinated graphene is synthesized based on direct gas fluorination and plasma fluorination [10,12,16], which, however, require tedious multiple steps, harsh experimental conditions, and high energy consumption.

In the present study, we have demonstrated a facile one-pot approach for the synthesis of FGO from graphite. The resulting FGO was systematically characterized using field-emission scanning electron microscope (FE-SEM), X-ray diffractometer (XRD), Fourier transform infrared (FTIR) spectroscopy, Raman spectroscopy, and X-ray photoelectron spectroscopy (XPS). Further, we have investigated the electrochemistry of FGO, and a distinct behavior was observed when FGO was used in comparison to GO for heavy metal ion stripping.

SUMMARY OF THE INVENTION

According to a first aspect of the invention, there is provided a method for synthesis of about 0.5 to about 1.5 at. % fluorinated graphene oxide comprising:

mixing n grams of graphite with about 5*n to about 40*n ml HF in a solution of about 50*n to about 150*n ml of $H_2SO_4/H_3PO_4$ (10-x:x, where x is equal to 0.1 to 4) with stirring at a temperature of about 30 to about 80° C. for a first period of time;

adding about 3*n to about 10*n g $KMnO_4$ to the mixture and stirring the mixture at a temperature of about 40 to about 80° C. for a second period of time;

adding the reacted mixture to a container containing about 50*n to about 250*n ml of ice and about 1*n to about 10*n ml of $H_2O_2$;

separating solid comprising about 0.5 to about 1.5 at. % fluorinated graphene oxide from the mixture;

rinsing the fluorinated graphene oxide; and drying the fluorinated graphene oxide.

The first time period may be about 1 to about 5 hours.

The second time period may be about 5 to 50 hours.

In some embodiments, the fluorinated graphene oxide is rinsed with HCl, then water, then ethanol and then diethyl ether.

BRIEF DESCRIPTION OF THE DRAWINGS

FIG. 1. (A) & (B) SEM images of graphene oxide (GO) and fluorinated graphene oxide (FGO). (C) TEM image of FGO. Inset shows the SAED pattern of FGO. (D) XRD patterns of graphite, GO and FGO.

FIG. 2. (A) FT-IR spectra of graphite, GO and FGO. (B) Raman spectra of GO and FGO. (C) XPS survey scan of GO and FGO. (D) & (E) High resolution XPS spectra of C1s of GO and FGO. (F) High resolution the XPS spectrum of F1s of FGO.

FIG. 3. (A) CVs of GO and FGO modified GCE electrode in the acetate buffer. (B) SWASVs for 2 μM analytes each of Cd(II), Pb(II), Cu(II), Hg(II) on FGO (blue line), GO (red line) and GCE (black line). (C) SWASVs of FGO for Cd(II) sensing & inset is the calibration curve. (D) SWASVs of FGO for Pb(II) sensing & inset is the corresponding calibration curve. (E) SWASVs of FGO for the simultaneous sensing of Cd(II), Pb(II), Cu(II), Hg(II). (F) Calibration plots for the electrochemical detection of Cd(II), Pb(II), Cu(II) and Hg(II) ions.

DESCRIPTION OF THE PREFERRED EMBODIMENTS

Unless defined otherwise, all technical and scientific terms used herein have the same meaning as commonly understood by one of ordinary skill in the art to which the invention belongs. Although any methods and materials similar or equivalent to those described herein can be used in the practice or testing of the present invention, the preferred methods and materials are now described. All publications mentioned hereunder are incorporated herein by reference.

As used herein in the specification and claims, any numerical range recited herein is intended to include all sub-ranges subsumed therein.

In the present description, where used or otherwise designated to apply as described above, the terms “about” means ±20% of the indicated range or value unless otherwise indicated.

As discussed herein, in this method fluorine (heteroatom) doping and oxidation of graphite occurs simultaneously. Controlled fluorine doping and semi ionic nature of the C—F bond are the specialty of this process.

In other methods, reported in literature, a minimum of two steps are involved, specifically, oxidation of graphite then fluorination. Graphite is oxidized using a known method such as modified hummers method then fluorination performed by hydrothermal [17] and direct heating in $F_2$ atmosphere [16,18]. Fluorinating agents used are $XeF_2$, $F_2$, HF and Hexafluorophosphoric acid. Alternatively fluorinated graphene oxide also produced from fluorinated graphite via chemical treatment [19] and mechanical exfoliation [20]. Here fluorination of graphite is first step then exfoliation and oxidation is second step.

In the method described herein, as the fluorinating agent is added at the beginning of oxidation process. Fluorinating agent facilitates the oxidation of graphite and introducing fluorine on graphene sheets. In one step oxidation as well as doping of fluorine accomplished in this method.

Prior art methods reported for preparation of fluorinated graphene oxide are employed harsh experimental conditions and require multiples steps. In order to simplify the method, we have developed in-situ doping of graphene oxide by adding the fluorinating agent to the oxidation mixture. The results have shown that we successfully incorporated ~1.2 at. % fluorine content in graphene oxide which is semi-ionically bonded with carbon. This allows for simultaneous oxidation and functionalization of graphite using wet chemical synthesis.

Doping and functionalization could significantly assist in the improvement of the electrochemical properties of graphene derivatives. Herein, we report a one-pot synthesis of fluorinated graphene oxide (FGO) from graphite. The surface morphology, functionalities and composition of the resulting FGO have been studied using various surface characterization techniques, revealing that layer-structured nanosheets with ~1.0 at. % F were formed. The carbon bound F exhibited semi-ionic bonding characteristic and significantly increased the capacitance of FGO compared to graphene oxide (GO). Further, the FGO has been employed for the simultaneous detection of heavy metal ions $Cd^{2+}$, $Pb^{2+}$, $Cu^{2+}$ and $Hg^{2+}$ using square wave anodic stripping voltammetry; and a substantial improvement in the electrochemical sensing performance is achieved in comparison with GO.

As discussed herein, we have demonstrated a facile one-pot synthesis method for the preparation of GO and FGO. Their compositions, morphology, and structure were investigated, revealing that FGO possessed a higher amount and different proportions of functional groups than GO. The presence of fluorine was confirmed by XPS, and Raman spectra analysis; and the fluorine content was estimated as ~1.0 at. %. After the electrochemical reduction, FGO exhibited a much higher specific capacitance than GO. For the first time, heavy metal ion stripping was demonstrated on metal-free FGO with a high sensitivity. The novel one-pot synthesis of the fluorine doped graphene oxide described in this study opens the door to develop various halogenated graphene derivatives for energy, environmental and electrochemical sensing applications.

As will be known to one of skill in the art, a high amount of fluorination causes wettability and conductivity issues. In contrast, as discussed herein, a fluorine content at ~1.0 at. % improves the structural and electrochemical properties of FGO compared to GO. In general, highly fluorinated graphene exhibits amphiphobic and insulating properties, which is not good for electrochemical applications. Hence, a few percentages of fluorine doped graphene is useful for tunable electrochemical properties. For example, as discussed herein, the FGO can be used as a sensor, for energy storage, for catalyst support or for other uses which will be apparent to one of skill in the art.

For example, a sensor study demonstrated the applicability of the present system for heavy metal ion detection.

Using the method described herein, we obtained up to 1.5% fluorine content in the synthesised FGO. As discussed herein, this ~0.5-1.5 at. % FGO is useful in various electrochemical applications such as energy storage, energy conversion, and sensor applications.

According to an aspect of the invention, there is provided a method for synthesis of about 0.5 to about 1.5 at. % fluorinated graphene oxide comprising:

mixing about n grams of graphite with about 5*n to about 40*n ml HF in a solution of about 70*n to about 150*n ml of $H_2SO_4/H_3PO_4$ (10-x:x, where x=0.1 to 4) with stirring at a temperature of about 30 to about 80° C. for a first period of time;

adding about 3*n to about 10*n g $KMnO_4$ to the mixture and stirring the mixture at a temperature of about 40 to about 80° C. for a second period of time;

adding the reacted mixture to a container containing about 50*n to about 250*n ml of ice and about 1*n to about 10*n ml of $H_2O_2$;

separating solid comprising about 0.5 to about 1.5 at. % fluorinated graphene oxide from the mixture;

rinsing the fluorinated graphene oxide; and drying the fluorinated graphene oxide.

The first time period may be about 1 to 5 hours.

The second time period may be about 5 to 50 hours.

In some embodiments, the fluorinated graphene oxide is rinsed with HCl, then water, then ethanol and then diethyl ether.

As discussed herein, the FGO of the invention can be used as a sensor, for energy storage, for catalyst support or for other uses which will be apparent to one of skill in the art.

FIGS. 1A & B display the SEM images, where similar wrinkled layered structure was observed for both GO and FGO, indicating that the addition of HF in the improved method did not affect the overall oxidation and exfoliation of graphite. The TEM image of FGO (FIG. 1C) also confirmed the intrinsic folds and transparent layered structure of the exfoliated sheets. The selected area electron diffraction (SAED) pattern of the FGO (Inset of FIG. 1C) exhibited a weak hexagonal structure that was indicative of severe exfoliation. Further, the XRD pattern of FGO compared with GO and the graphite is illustrated in FIG. 1D. Graphite showed a characteristic (002) peak at ~26.42° corresponding to interlayer spacing (d) of 0.337 nm and crystallite size (Lc) of 20.83 nm. In contrast, the graphitic peak disappeared; instead the characteristic 2θ peaks at 10.53° and 10.81° were observed for the FGO and GO, respectively, showing that graphite was completely oxidized. Further, the interlayer distance was calculated from the 2θ peak to be 0.839, and 0.818 nm for FGO and GO, respectively; The slightly larger interlayer distance may be attributed to the C—F formation and its repulsive effect [18].

Figure 2:
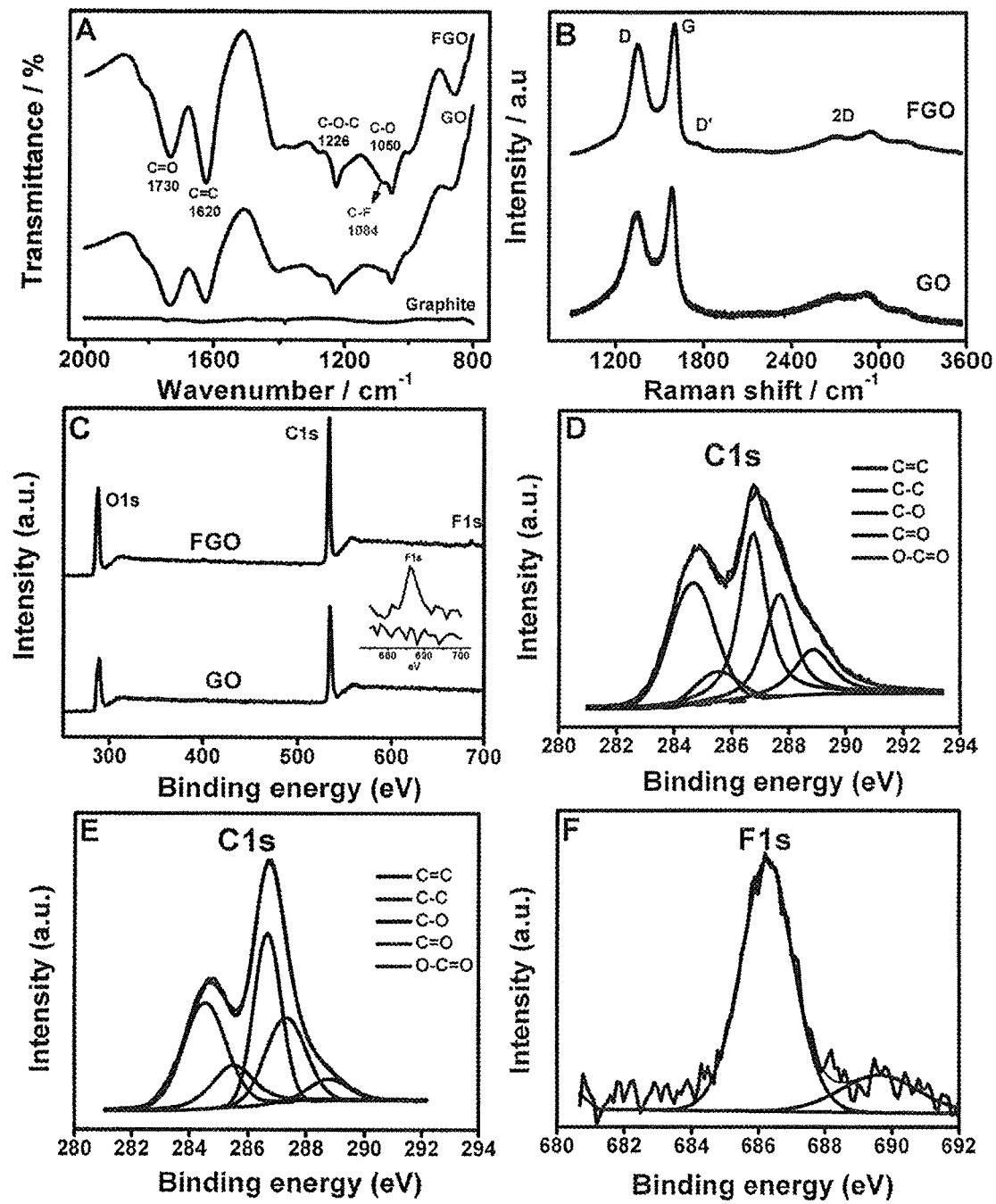

FIG. 2A presents the FTIR spectra of FGO and GO, where several characteristic peaks for various functional groups such as C—O group (1060 $cm^{-1}$), carbonyl (C=O, 1730 $cm^{-1}$), C=C (1620 $cm^{-1}$), epoxy (C—O—C, 1228 $cm^{-1}$) were observed for both GO and FGO. However, FGO had an additional peak at 1083 $cm^{-1}$, which can be attributed to the semi-ionic C—F bond [15,21]. In addition, the ratio of the C=O bond to the C=C bond was slightly decreased due to the formation of the C—F functional group in the FGO. Furthermore, as shown in FIG. 2B, although the Raman spectra of FGO and GO were similar, the G band was shifted from 1582 $cm^{-1}$ for GO to 1599 $cm^{-1}$ for FGO, indicating that it possessed fewer layers than the GO, which is consistent with the SEM images displayed in FIGS. 1A and 1B. Additionally, the $I_D/I_G$ ratio of FGO was calculated to be 0.84, which was higher than that of GO (0.82), indicating that fluorination caused more defects. Also, the D' peak appeared in FGO, which was not present in GO, further confirming fluorination. All the aforementioned observations indicated that the addition of HF in the oxidative treatment could effectively exfoliate the graphene layers and generated a high degree of disorder in the resulting FGO. XPS was also employed to characterize the composition and types of functional groups in FGO and GO. As seen in the enlarged portion of the XPS survey scans (FIG. 2C), the existence of fluorine was confirmed by the appearance of the F peak at ~686.37 eV. The composition of FGO was calculated to be 65.20% C, 33.64% O, and 1.16% F; whereas the composition of GO was estimated to be 65.17% C and 34.83% O. FIG. 2D presents the high resolution C1s spectrum of GO, showing two major peaks, which were deconvoluted into five peaks: C$\alpha$C (284.5 eV), C—C (285.5 eV), C—O (286.7 eV), C=O (287.6 eV), and O—C=C (288.7 eV). As shown in the C1s spectrum of FGO (FIG. 2E), notable changes were observed in terms of peak intensities when compared with the C1s spectrum of GO. The C=O and O—C=O content were diminished in FGO, while the C—O content was increased, due to the F attack of the C=O group and the formation of C—O and C—F bond. This was further confirmed by the high resolution F1s spectrum of FGO (FIG. 2F), where the main peak (686.25 eV) was attributed to the semi-ionic nature C—F bond and the shoulder peak centred at 689.62 eV corresponded to the covalent C—F bond [12].

Figure 3:
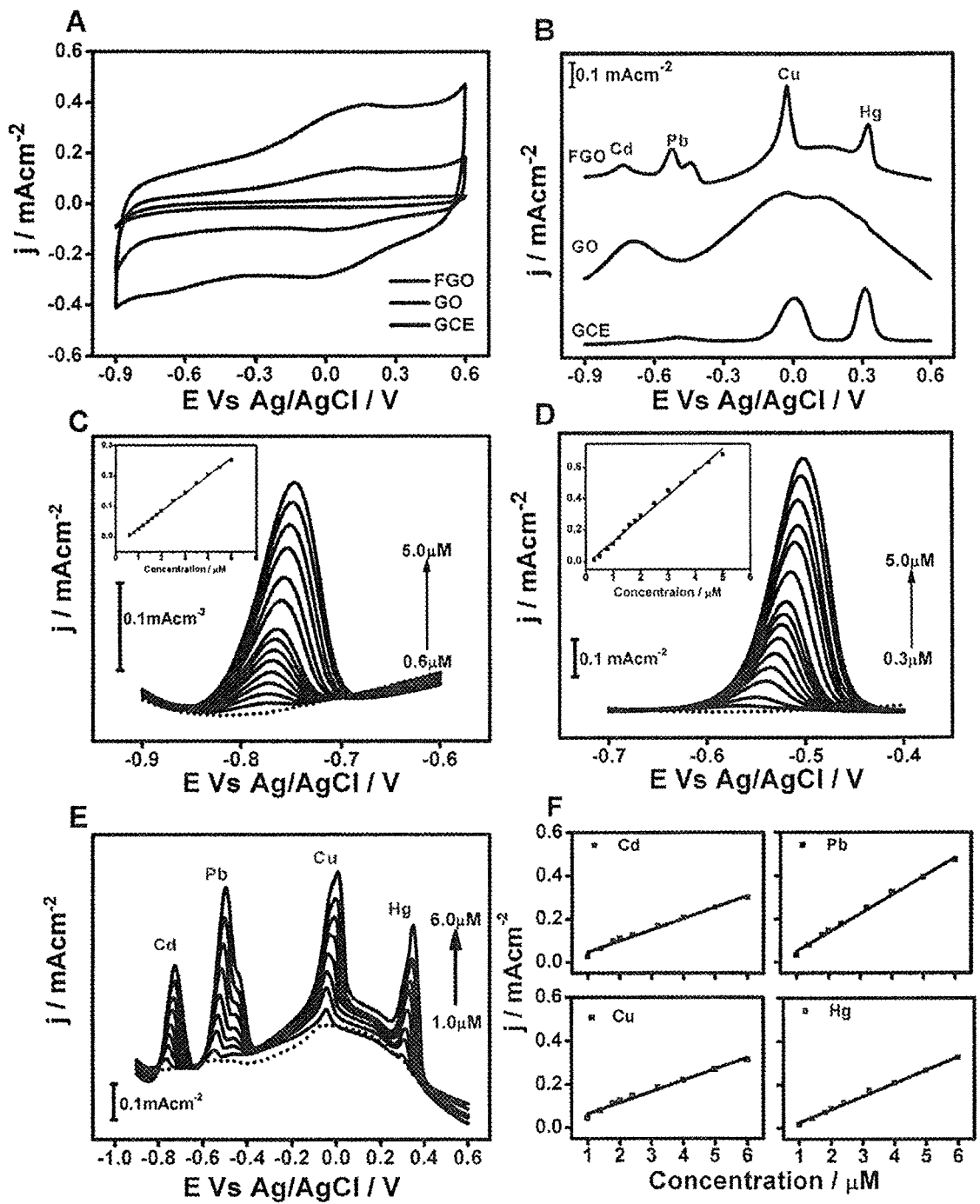

Functionalities of a carbon surface may assist the heavy metal ion adsorption properties [22]. To improve their conductivity, FGO and GO were electrochemically reduced at −1.2 V for 300 s in a 0.1 M acetate buffer (pH=5.0). FIG. 3A presents the CVs of the GCE (substrate), and the electrochemical pre-treated FGO and GO recorded in the acetate buffer, showing a dramatic difference in the capacitance of the three electrodes, which may be estimated using the following equation [23]:

$$C=A/(2\times\Delta E\times v\times m)$$

where A—the integrated area of CV; $\Delta E$—the potential window; v—the scan rate; and m—the mass of the GO or FGO. After the pretreatment, the capacitance of FGO was calculated to be 94.22 F g$^{-1}$, which was much higher than that of GO (32.75 F g$^{-1}$).

Simultaneous electrochemical sensing of heavy metal ions was carried out as displayed in FIG. 3B, where 2.0 μM of each metal ion was used for comparison. No notable stripping currents were seen for Cd and Pb at the GCE; and overlapped broad peaks were observed at GO, indicating that the stripping may not be easily achieved, due to the strong bonding of metal ions to the GO surface [24]. In contrast, the FGO showed significant currents for all the four heavy metal ions with distinguishable peaks.

Thus, the low fluorine-content FGO described herein exhibited applicability towards simultaneous heavy metal ion sensing. It was noticed that Pb stripping had doublet peak, which may be due to the complexing mechanism with other metal ions [25,26], and that Cd had the smallest current response compared to other three metal ions. Hence, individual detection of Cd and Pb was carried out to confirm the sensitivity and complexing mechanism, as displayed in FIGS. 3C and 3D. For Cd, a linear current response range was obtained from 0.6 μM to 5.0 μM ($R^2$=0.9987) with a high sensitivity of 4.06 μA μM$^{-1}$ and the calculated lowest detection limit (LOD) of 10 nM. In the case of Pb, a single peak was observed, confirming that the double peak was due to the complex formation in presence of other metal ions. A linear current response range was attained from 0.3 μM to 5.0 μM ($R^2$=0.9922) with a very high sensitivity of 10.32 μA μM$^{-1}$ and the LOD of 10 nM.

Simultaneous sensing of four metal ions on FGO was performed with concentrations varying from 1.0 to 6.0 μM, and the SWASV curves and corresponding calibration plots are presented in FIGS. 3E and 3F, respectively. All the four metals were stripped with appropriate potential intervals and the stripping currents increased proportionally with the increase of their concentration. The correlation factors ($R^2$) obtained from the calibration plots were 0.9881, 0.9951, 0.9879 and 0.9922 for Cd, Pb, Cu and Hg, respectively. Sensitivity of the simultaneous detection of each metal ion was determined to be 3.64, 6.05, 3.64 and 4.24 μA μM$^{-1}$ for Cd, Pb, Cu and Hg, respectively.

Materials and Methods

High purity graphite powder (Albany graphite deposit) was provided by Zenyatta Ventures Ltd. Sulfuric acid (98%), hydrofluoric acid (50%), copper(II) nitrate trihydrate (99.0%), mercury(II) nitrate monohydrate (≥98.5%), and lead(II) nitrate (≥99.0%) were sourced from Sigma Aldrich. Analytical grade reagents (phosphoric acid (85%), potassium permanganate (≥99.0%), potassium chloride (99.0), acetic acid (≥99.7%), sodium acetate (≥99.0%) and cadmium(II) nitrate tetra hydrate (98%)) were used as received without further purification. Pure water (18.2 MΩ cm, Nanopure® diamond™ UV water purification system) was used for aqueous solution preparation.

FGO was synthesized by the improved Hummers' method with some modifications [27]. Briefly, 1 g of graphite was added in the mixture of 90 ml $H_2SO_4$, 10 ml $H_3PO_4$, and 20 ml HF. After vigorous stirring at 50° C. for two hours, 4.5 g of $KMnO_4$ was added slowly into the reaction mixture and was stirred continuously for another 15 hours. Then 100 ml ice was added to the reaction mixture followed by an addition of 5 ml of 30% $H_2O_2$. The resulting FGO was separated and rinsed with 30% HCl, pure water, ethanol, and diethyl ether. Finally, the resulting yellowish brown solid was dried in the oven at 50° C. For comparison, GO was also prepared using the same procedure, but without the addition of HF.

Morphological studies and surface characterization were conducted using FE-SEM (Hitachi SU-70), TEM (JOEL 2010), XRD (Panalytical Instrument), FTIR spectrometer (Thermo scientific), Raman spectroscopy, XPS (Thermo scientific). Cyclic voltammetry (CV) and square wave voltammetry (SWV) were conducted using a CHI 660E electrochemical workstation. A 2.5 mg sample of FGO or GO was dispersed in 1 ml of isopropanol-water (1:1) mixture using ultrasonication for 30 minutes. Then a 3 μL aliquot of the FGO or GO dispersed solution was drop-cast on a polished glassy carbon electrode (GCE) surface and dried. The FGO/GCE and GO/GCE were pretreated electrochemically at a constant potential −1.2 V vs Ag/AgCl in a 0.1 M acetate buffer solution (pH 5.0). Two steps were involved in the heavy metal ion sensing: (i) deposition of metal ions at −0.9 V for 175 s; and (ii) square wave anodic stripping voltammetry (SWASV) conducted from −0.9 to 0.6 V.

The scope of the claims should not be limited by the preferred embodiments set forth in the examples but should be given the broadest interpretation consistent with the description as a whole.

REFERENCES

[1] X. Jia, J. Campos-Delgado, M. Terrones, V. Meunier, M. S. Dresselhaus, Graphene edges: a review of their fabrication and characterization., Nanoscale. 3 (2011) 86-95.
[2] J. Duan, S. Chen, M. Jaroniec, S. Z. Qiao, Heteroatom-Doped Graphene-Based Materials for Energy-Relevant Electrocatalytic Processes, ACS Catalysis. 5 (2015) 5207-5234.
[3] V. Georgakilas, M. Otyepka, A. B. Bourlinos, V. Chandra, N. Kim, K. C. Kemp, P. Hobza, R. Zboril, K. S. Kim, Functionalization of Graphene: Covalent and Non-Covalent Approaches, Derivatives and Applications, Chemical Reviews. 112 (2012) 6156-6214.
[4] B. Zheng, J. Wang, F. B. Wang, X. H. Xia, Synthesis of nitrogen doped graphene with high electrocatalytic activity toward oxygen reduction reaction, Electrochemistry Communications. 28 (2013) 24-26.
[5] A. Vizintin, M. Lozinšek, R. K. Chellappan, D. Foix, A. Krajnc, G. Mali, G. Drazic, B. Genorio, R. Dedryvére, R. Dominko, Fluorinated Reduced Graphene Oxide as an Interlayer in Li—S Batteries, Chemistry of Materials. 27 (2015) 7070-7081.
[6] H. L. Poh, P. Šimek, Z. Sofer, M. Pumera, Halogenation of graphene with chlorine, bromine, or iodine by exfoliation in a halogen atmosphere, Chemistry—A European Journal. 19 (2013) 2655-2662.
[7] J. Han, L. L. Zhang, S. Lee, J. Oh, K. S. Lee, J. R. Potts, J. Ji, X. Zhao, R. S. Ruoff, S. Park, Generation of B-doped graphene nanoplatelets using a solution process and their supercapacitor applications, ACS Nano. 7 (2013) 19-26.
[8] H. L. Poh, P. Šimek, Z. Sofer, M. Pumera, Sulfur-doped graphene via thermal exfoliation of graphite oxide in H 2S, SO2, or CS2 gas, ACS Nano. 7 (2013) 5262-5272.
[9] K. J. Jeon, Z. Lee, E. Pollak, L. Moreschini, A. Bostwick, C. M. Park, R. Mendelsberg, V. Radmilovic, R. Kostecki, T. J. Richardson, E. Rotenberg, Fluorographene: A wide band-gap semiconductor with ultraviolet luminescence, ACS Nano. 5 (2011) 1042-1046.
[10] L. Cheng, S. Jandhyala, G. Mordi, A. T. Lucero, J. Huang, A. Azcatl, R. Addou, R. M. Wallace, L. Colombo, J. Kim, Partially Fluorinated Graphene: Structural and Electrical Characterization, ACS Applied Materials & Interfaces. 8 (2016) 5002-5008.
[11] R. Gusmão, Z. Sofer, F. Šembera, Z. Janoušek, M. Pumera, Electrochemical Fluorographane: Hybrid Electrocatalysis of Biomarkers, Hydrogen Evolution, and Oxygen Reduction, Chemistry—A European Journal. 21 (2015) 16474-16478.
[12] W. Feng, P. Long, Y. Feng, Y. Li, Two-Dimensional Fluorinated Graphene: Synthesis, Structures, Properties and Applications, Advanced Science. 3 (2016) 1500413.
[13] D. Damien, P. M. Sudeep, T. N. Narayanan, M. R. Anantharaman, P. M. Ajayan, M. M. Shaijumon, Fluorinated graphene based electrodes for high performance primary lithium batteries, RSC Advances. 3 (2013) 25702.
[14] R. Romero-Aburto, T. N. Narayanan, Y. Nagaoka, T. Hasumura, T. M. Mitcham, T. Fukuda, P. J. Cox, R. R. Bouchard, T. Maekawa, D. S. Kumar, S. V. Tot, S. A. Mani, P. M. Ajayan, Fluorinated graphene oxide; A new multimodal material for biological applications, Advanced Materials. 25 (2013) 5632-5637.
[15] F.-G. Zhao, G. Zhao, X.-H. Liu, C.-W. Ge, J.-T. Wang, B.-L. Li, Q.-G. Wang, W.-S. Li, Q.-Y. Chen, Fluorinated graphene: facile solution preparation and tailorable properties by fluorine-content tuning, Journal of Materials Chemistry A. 2 (2014) 8782-8789.
[16] X. Wang, Y. Dai, J. Gao, J. Huang, B. Li, C. Fan, J. Yang, X. Liu, High-yield production of highly fluorinated graphene by direct heating fluorination of graphene-oxide, ACS Applied Materials and Interfaces. 5 (2013) 8294-8299.
[17] X. Yang, X. Jia, X. Ji, Acid induced fluorinated graphene oxide, RSC Adv. 5 (2015) 9337-9340.
[18] O. Jankovský, P. Šimek, D. Sedmidubský, S. Matějková, Z. Janoušek, F. Šembera, M. Pumera, Z. Sofer, Water-soluble highly fluorinated graphite oxide, RSC Advances. 4 (2014) 1378.
[19] A. Mathkar, T. N. Narayanan, L. B. Alemany, P. Cox, P. Nguyen, G. Gao, P. Chang, R. Romero-Aburto, S. A. Mani, P. M. Ajayan, Synthesis of fluorinated graphene oxide and its amphiphobic properties, Part. Part. Syst. Charact. 30 (2013) 266-272.
[20] M. Inagaki, F. Y. Kang, Graphene derivatives: graphane, fluorographene, graphene oxide, graphyne and graphdiyne, J. Mater. Chem. A. 2 (2014) 13193-13206.
[21] L. Pu, Y. Ma, W. Zhang, H. Hu, Y. Zhou, Q. Wang, C. Pei, Simple method for the fluorinated functionalization of graphene oxide, RSC Advances. 3 (2013) 3881.
[22] Y.-F. Sun, L.-J. Zhao, T.-J. Jiang, S.-S. Li, M. Yang, X.-J. Huang, Sensitive and selective electrochemical detection of heavy metal ions using amino-functionalized carbon microspheres, J. Electroanal. Chem. 760 (2016) 143-150.
[23] W. Chen, Z. Fan, L. Gu, X. Bao, C. Wang, Enhanced capacitance of manganese oxide via confinement inside carbon nanotubes, Chem. Commun. 46 (2010) 3905-3907.
[24] J. G. S. Moo, B. Khezri, R. D. Webster, M. Pumera, Graphene oxides prepared by Hummers', Hofmann's, and Staudenmaier's methods: dramatic influences on heavymetal-ion adsorption, Chem Phys Chem 15 (2014) 2922-2929.
[25] Y. Wei, C. Gao, F.-L. Meng, H.-H. Li, L. Wang, J.-H. Liu, X.-J. Huang, $SnO_2$/reduced graphene oxide nanocomposite for the simultaneous electrochemical detection of cadmium(II), lead(II), copper(II), and mercury(II): an interesting favorable mutual interference, J. Phys. Chem. C 116 (2012) 1034-1041.
[26] Y. L. Xie, S. Q. Zhao, H. L. Ye, J. Yuan, P. Song, S. Q. Hu, Graphene/CeO2 hybrid materials for the simultaneous electrochemical detection of cadmium(II), lead(II), copper (II), and mercury(II), J. Electroanal. Chem. 757 (2015) 235-242.
[27] D. C. Marcano, D. V. Kosynkin, J. M. Berlin, A. Sinitskii, Z. Sun, A. Slesarev, L. B. Alemany, W. Lu, J. M. Tour, Improved Synthesis of Graphene Oxide, ACS Nano. 4 (2010) 4806-4814.

The invention claimed is:
1. A method for synthesis of about 0.5 to about 1.5 at. % fluorinated grapheme oxide comprising:
   mixing about n grams of graphite with about 5*n to about 40*n ml HF in a solution of about 50*n to about 150*n ml of $H_2SO_4/H_3PO_4$ at a ratio of 10-x:x, where x=0.1 to 4 with stirring at a temperature of about 30 to about 80° C. for a first period of time to generate a first mixture;
   adding about 3*n to about 10*n g $KMnO_4$ to the first mixture to generate a second mixture and stirring the second mixture at a temperature of about 40 to about 80° C. for a second period of time;
   adding the second mixture to a container containing about 50*n to about 250*n ml of ice and about 1*n to about 10*n ml of $H_2O_2$ to generate a third mixture;
   separating solid comprising about 0.5 to about 1.5 at. % fluorinated grapheme oxide from the third mixture;
   rinsing the fluorinated graphene oxide; and
   drying the fluorinated graphene oxide.

2. The method according to claim 1 wherein the first time period is about 1 to 5 hours.

3. The method according to claim 1 wherein the second time period is about 5 to about 50 hours.

4. A method for synthesis of about 0.5 to about 1.5 at. % fluorinated graphene oxide comprising:
- mixing about n grams of graphite with about 5*n to about 40*n ml HF in a solution of about 50*n to about 150*n ml of $H_2SO_4/H_3PO_4$ at a ratio of 10-x:x, where x=0.1 to 4 with stirring at a temperature of about 30 to about 80° C. for a first period of time to generate a first mixture;
- adding about 3*n to about 10*n g $KMnO_4$ to the first mixture to generate a second mixture and stirring the second mixture at a temperature of about 40 to about 80° C. for a second period of time;
- adding about 50*n to about 250*n ml of ice to the second mixture, followed by adding about 1*n to about 10*n ml of $H_2O_2$ to the second mixture to generate a third mixture;
- separating solid comprising about 0.5 to about 1.5 at. % fluorinated graphene oxide from the third mixture;
- rinsing the fluorinated graphene oxide; and
- drying the fluorinated graphene oxide.

5. The method according to claim 4 wherein the first time period is about 1 to about 5 hours.

6. The method according to claim 4 wherein the second time period is about 5 to about 50 hours.

\* \* \* \* \*